US00PP19164P2

(12) United States Plant Patent
Hofmann

(10) Patent No.: US PP19,164 P2
(45) Date of Patent: Sep. 2, 2008

(54) ***BIDENS* PLANT NAMED 'FISBIMEX'**

(50) Latin Name: *Bidens ferulifolia*
Varietal Denomination: Fisbimex

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 11/800,776

(22) Filed: May 7, 2007

(51) Int. Cl.
*A01H 5/00* (2006.01)

(52) U.S. Cl. ..... Plt./410
(58) Field of Classification Search ..... Plt./410
See application file for complete search history.

*Primary Examiner*—Annette H Para
(74) *Attorney, Agent, or Firm*—C. A. Whealy

(57) ABSTRACT

A new and distinct cultivar of *Bidens* plant named 'Fisbimex', characterized by its semi-upright, outwardly spreading to somewhat trailing plant habit; moderately vigorous to vigorous growth habit; early and freely flowering habit; large inflorescences with typically about eight dark yellow-colored ray florets; and moderately strong peduncles that hold the inflorescences above and beyond the foliar plane.

1 Drawing Sheet

Botanical designation: *Bidens ferulifolia.*
Cultivar denomination: 'Fisbimex'.

BACKGROUND OF THE INVENTION

The present invention relates to a new and distinct cultivar of *Bidens* plant, botanically known as *Bidens ferulifolia,* and hereinafter referred to by the name 'Fisbimex'.

The new *Bidens* originated from a cross-pollination made by the Inventor in Hillscheid, Germany during the summer of 2003, of the *Bidens ferulifolia* cultivar Marietta Gold, not patented, as the female, or seed, parent with the *Bidens ferulifolia* cultivar Golden Star, disclosed in U.S. Plant Pat. No. 12,589, as the male, or pollen, parent. The new *Bidens* was discovered and selected by the Inventor as a single flowering plant from within the progeny of the stated cross-pollination grown in a controlled environment in Hillscheid, Germany during the spring of 2004.

Asexual reproduction of the new *Bidens* by vegetative cuttings in a controlled environment in Hillscheid, Germany since the summer of 2004, has shown that the unique features of this new *Bidens* are stable and reproduced true to type in successive generations.

SUMMARY OF THE INVENTION

The cultivar Fisbimex has not been observed under all possible environmental conditions. The phenotype may vary somewhat with variations in environment such as temperature and light intensity, without, however, any variance in genotype.

The following traits have been repeatedly observed and are determined to be the unique characteristics of 'Fisbimex'. These characteristics in combination distinguish 'Fisbimex' as a new and distinct cultivar of *Bidens:*

1. Semi-upright, outwardly spreading to somewhat trailing plant habit.
2. Moderately vigorous to vigorous growth habit.
3. Early and freely flowering habit.
4. Large inflorescences with typically about eight dark yellow-colored ray florets.

5. Moderately strong peduncles that hold the inflorescences above and beyond the foliar plane.

Plants of the new *Bidens* differ from plants of the female parent, the cultivar Marietta Gold, in the following characteristics:

1. Plants of the new *Bidens* and the cultivar Marietta Gold differ in stem color.
2. Plants of the new *Bidens* have lighter green-colored leaves than plants of the cultivar Marietta Gold.
3. Plants of the new *Bidens* have larger inflorescences than plants of the cultivar Marietta Gold.
4. Plants of the new *Bidens* and the cultivar Marietta Gold differ in ray floret color.
5. Plants of the new *Bidens* have shorter peduncles than plants of the cultivar Marietta Gold.

Plants of the new *Bidens* differ from plants of the male parent, the cultivar Golden Star, in the following characteristics:

1. Plants of the new *Bidens* and the cultivar Golden Star differ in stem color.
2. Plants of the new *Bidens* have smaller leaves than plants of the cultivar Golden Star.
3. Plants of the new *Bidens* have larger inflorescences than plants of the cultivar Golden Star.
4. Inflorescences of plants of the new *Bidens* have more ray florets than inflorescences of plants of the cultivar Golden Star.

Plants of the new *Bidens* can be compared to plants of the *Bidens* cultivar Peters Goldteppich, disclosed in U.S. Plant Pat. No. 12,880. In side-by-side comparisons conducted in Hillscheid, Germany, plants of the new *Bidens* differed from plants of the cultivar Peters Goldteppich in the following characteristics:

1. Inflorescences of plants of the new *Bidens* had more ray florets than inflorescences of plants of the cultivar Peters Goldteppich.
2. Ray florets of plants of the new *Bidens* were darker yellow in color than ray florets of plants of the cultivar Peters Goldteppich.
3. Plants of the new *Bidens* had shorter peduncles than plants of the cultivar Peters Goldteppich.

BRIEF DESCRIPTION OF THE PHOTOGRAPHS

The accompanying photographs illustrate the overall appearance of the new *Bidens*. The photographs show the colors as true as it is reasonably possible to obtain in colored reproductions of this type. Colors in the photographs may differ slightly from the color values cited in the detailed botanical description which accurately describe the colors of the new *Bidens*.

The photograph at the top of the first sheet comprises a side perspective view of a typical flowering plant of 'Fisbimex' grown in a container.

The photograph at the bottom of the sheet is a close-up view of a typical inflorescence of 'Fisbimex'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Hillscheid, Germany during the winter in a glass-covered greenhouse and under conditions and practices which approximate those generally used in commercial *Bidens* production. During the production of the plants, day temperatures ranged from about 16° C. to 18° C. and night temperatures averaged 16° C. Plants were pinched one time when they were planted. Measurements and numerical values represent averages for typical flowering plants. Plants were about five months old when the photographs and description were taken.

Botanical classification: *Bidens ferulifolia* cultivar Fisbimex.

Parentage:

*Female parent.*—*Bidens ferulifolia* cultivar Marietta Gold, not patented.

*Male parent.*—*Bidens ferulifolia* cultivar Golden Star, disclosed in U.S. Plant Pat. No. 12,589.

Propagation:

*Type.*—By vegetative cuttings.

*Time to initiate roots, summer.*—About eight days at 22° C. to 24° C.

*Time to initiate roots, winter.*—About ten days at 21° C.

*Time to produce a rooted young plant, summer.*—About two weeks at 22° C. to 24° C.

*Time to produce a rooted young plant, winter.*—About three weeks at 21° C.

*Root description.*—Fine, fibrous; close to N155D in color.

*Rooting habit.*—Freely branching; moderately dense.

Plant description:

*Plant form/growth habit.*—Semi-upright, outwardly spreading to somewhat trailing plant habit. Moderately vigorous to vigorous growth habit. Freely branching habit with lateral branches potentially forming at every node.

*Plant height.*—About 24 cm.

*Plant diameter or spread.*—About 47 cm to 53 cm.

*Lateral branches.*—Length: About 27 cm to 30 cm. Diameter: About 2 mm to 3 mm. Internode length: About 2.5 cm to 3 cm. Aspect: Upright, outwardly spreading or slightly trailing. Strength: Moderately strong; flexible. Texture: Pubescent. Color: Between 182B and 183C to 183D.

Foliage description:

*Arrangement.*—Opposite, decussate.

*Length.*—About 2.5 cm to 3 cm.

*Width.*—About 2.2 cm to 2.5 cm.

*Shape.*—Roughly deltoid; pinnatisect.

*Apex.*—Acute.

*Base.*—Acute to obtuse.

*Margin.*—Deeply incised.

*Texture, upper surface.*—Smooth glabrous.

*Texture, lower surface.*—Pubescence along veins.

*Venation pattern.*—Pinnate.

*Color.*—Developing foliage, upper surface: Between 143A and 137D. Developing foliage, lower surface: 138B. Fully expanded foliage, upper surface: 137B to 137C; venation, 137B to 137C. Fully expanded foliage, lower surface: 138B; venation, 138A.

*Petiole length.*—About 5 mm to 10 mm.

*Petiole diameter.*—About 1 mm to 1.5 mm.

*Petiole texture, upper surface.*—Smooth, glabrous.

*Petiole texture, lower surface.*—Pubescent.

*Petiole color, upper surface.*—Close to 138C.

*Petiole color, lower surface.*—Close to 138D.

Inflorescence description:

*Appearance.*—Rotate inflorescences form with ray and disc florets. Inflorescences positioned above the foliage on moderately strong peduncles. Inflorescences face mostly upright. Freely flowering habit; about 30 to 40 inflorescences developing per plant. Inflorescences persistent. Inflorescences not fragrant.

*Time to flower.*—Under natural season conditions, plants flower continuously from spring until the fall in Germany. Early flowering habit, plants begin flowering about 40 days after planting.

*Inflorescence bud.*—Height: About 9 mm. Diameter: About 7 mm. Shape: Ovoid. Color: 6A.

*Inflorescence size.*—Diameter: About 3.5 cm to 4.5 cm. Depth (height): About 7 mm. Disc diameter: About 8 mm. Receptacle diameter: About 3 mm to 5 mm. Receptacle height: About 3 mm to 4 mm.

*Ray florets.*—Shape: Ligulate to elliptical. Length: About 1.8 cm to 2 cm. Width, at apex: About 9 mm to 10 mm. Apex: Obtuse to dentate/praemorse. Base: Fused. Margin: Entire. Texture, upper and lower surfaces: Smooth, glabrous. Number of ray florets per inflorescence: About eight arranged in a single whorl. Color: When opening, upper surface: Close to 12B. When opening, lower surface: Close to 6B. Fully opened, upper surface: Close to 12A. Fully opened, lower surface: Close to 9A.

*Disc florets.*—Shape: Tubular; apex dentate. Length: About 3 mm to 4 mm. Diameter: About 1 mm. Number of disc florets per inflorescence: About 30. Color, immature: Apex: Close to N144B. Mid-section and base: Close to 150B. Color, mature: Apex: Close to 2A. Mid-section: Close to 2B. Base: Close to 2D.

*Phyllaries.*—Quantity per inflorescence: About 10 to 14 in two or three whorls. Length: About 6 mm to 7 mm. Width: About 1 mm to 1.5 mm. Shape: Lanceolate. Apex: Acute. Base: Fused. Margin: Entire. Texture, upper surface: Smooth, glabrous. Texture, lower surface: Pubescent. Color, upper surface: Close to 137A. Color, lower surface: Close to 137C.

*Peduncles.*—Length: About 3 cm to 5 cm. Diameter: About 1 mm to 2 mm. Strength: Moderately strong; flexible. Aspect: Slanting upright holding inflorescences above and beyond the foliage. Texture: Smooth, glabrous. Color: Close to 143D.

*Reproductive organs.*—Androecium: Quantity per disc floret: One. Anther shape: Linear. Anther length: About 4 mm to 5 mm. Anther color: Close to 200A. Pollen amount: Moderate. Pollen color: Close to 13A. Gynoecium: Pistil length: About 8 mm. Stigma shape: Cleft; reflexed. Stigma color: Close to 13B. Style length: About 4 mm. Ovary color: Close to 157D.

*Seeds.*—Quantity per inflorescence: About 25. Length: About 8 mm. Diameter: About 1 mm. Color: Mostly 200A.

Disease/pest resistance: Plants of the new *Bidens* have not been shown to be resistant to pathogens and pests common to *Bidens*.

Garden performance: Plants of the new *Clematis* have exhibited good tolerance to rain and wind and have been observed to tolerate temperatures from about 5° C. to about 35° C.

It is claimed:

1. A new and distinct *Bidens* plant named 'Fisbimex' as illustrated and described.

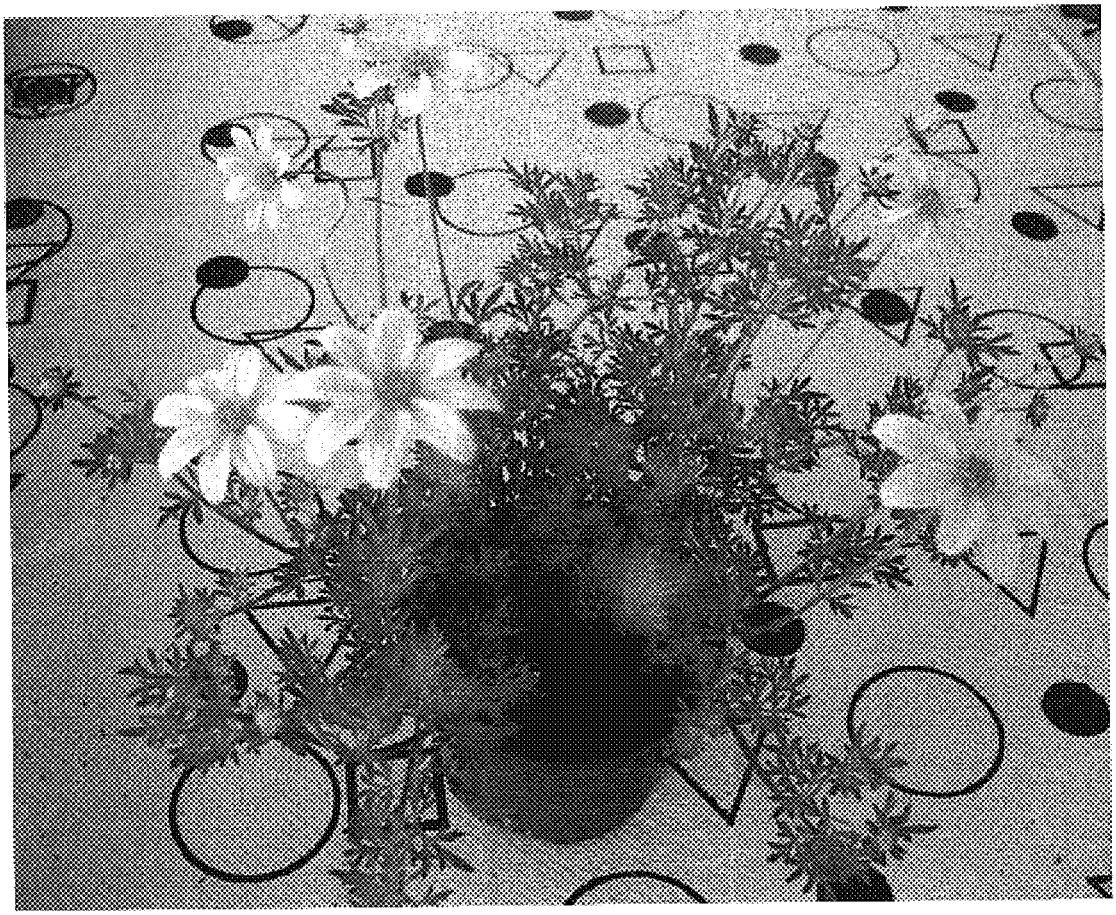
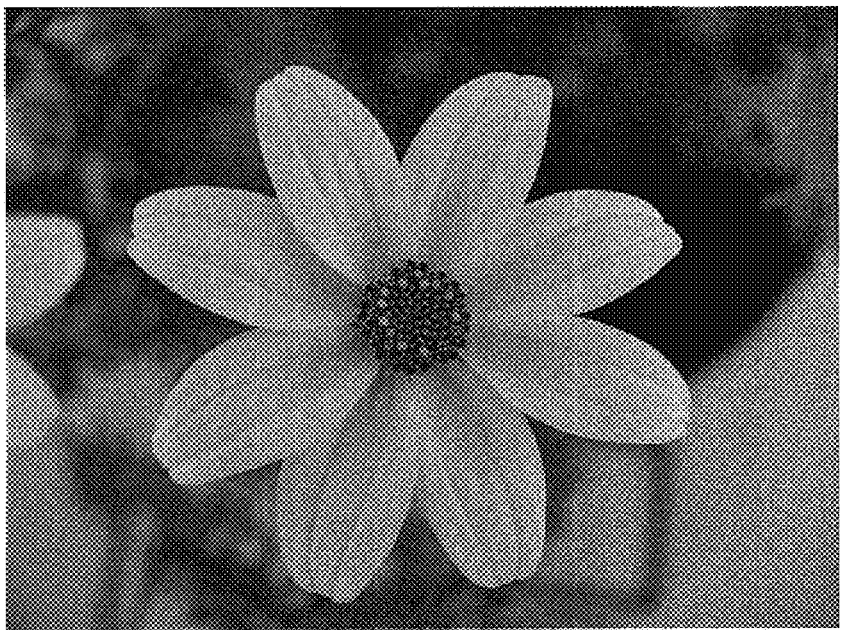

* * * * *